United States Patent
Vibert et al.

(10) Patent No.: US 9,126,917 B2
(45) Date of Patent: Sep. 8, 2015

(54) METHOD FOR PURIFYING VANILLIN BY LIQUID-LIQUID EXTRACTION

(71) Applicant: RHODIA OPERATIONS, Paris (FR)

(72) Inventors: Martine Vibert, Lyons (FR); Corine Cochennec, Voiron (FR); Alain Etchebarne, Melle (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/364,316

(22) PCT Filed: Dec. 13, 2012

(86) PCT No.: PCT/EP2012/075456
§ 371 (c)(1),
(2) Date: Jun. 11, 2014

(87) PCT Pub. No.: WO2013/087795
PCT Pub. Date: Jun. 20, 2013

(65) Prior Publication Data
US 2014/0316165 A1    Oct. 23, 2014

(30) Foreign Application Priority Data

Dec. 15, 2011 (FR) ..................... 11 61681

(51) Int. Cl.
*C07C 45/80* (2006.01)

(52) U.S. Cl.
CPC ..................... *C07C 45/80* (2013.01)

(58) Field of Classification Search
CPC ........................................ C07C 45/80
USPC ........................................ 568/324
See application file for complete search history.

(56) References Cited

U.S. PATENT DOCUMENTS

| | | | |
|---|---|---|---|
| 4,021,493 A | 5/1977 | Major et al. | |
| 6,133,003 A | 10/2000 | Rabenhorst et al. | |
| 2012/0103786 A1 | 5/2012 | Gayet et al. | |

FOREIGN PATENT DOCUMENTS

| | | |
|---|---|---|
| CN | 1250083 A | 4/2000 |
| EP | 0761817 A2 | 8/1996 |
| WO | WO 2010/007161 A1 | 1/2010 |

OTHER PUBLICATIONS

[Unknown Author]—Regulation (EC) No. 1334/2008 of European Parliament and of the Council of Dec. 16, 2008 on flavourings and certain food ingredients with flavouring properties for use in and on foods and amending Council Regulation (EEC) No. 1601/91, Regulations (EC) No. 2232/96 and (EC) No. 110/2008 and Directive 2000/13/EC, published in the Official Journal of the European Union on Dec. 31, 2008, L 354/34 to L 354/50 (17 pages), retrieved on Jun. 9, 2014 at http://www.fsai.ie/uploadedFiles/Reg%201334_2008.pdf.

[Unknown Author], Commission Directive 2009/32/EC of the European Parliament and of the Council of Apr. 23, 2009 on the approximation of the laws of the Member States on extraction solvents used in the production of foodstuffs and food ingredients, , published in the Official Journal of the European Union on Jun. 6, 2009, L 141/3 to L 141/11 (9pages), retrieved online on Jun. 9, 2014 at http://www.fsai.ie/uploadedFiles/Dir2009_32.pdf.

[Unknown Author], Commission Directive 2010/59/EU of Aug. 26, 2010 amending Directive 2009/32/EC of the European Parliament and of the Council on the approximation of the laws of the Member States on extraction, published in the Official Journal of the European Union on Aug. 27, 2010, L 225/10 to L225/12 (3 pages), retrieved online on Jun. 9, 2014 at https://www.fsai.ie/uploadedFiles/Dir2010_59.pdf.

*Primary Examiner* — Sikarl Witherspoon

(57) ABSTRACT

A method is described for purifying vanillin, and derivatives thereof, from an initial solution of vanillin or of a vanillin derivative in a solvent S1 containing impurities, comprising the following steps: a) a step of evaporating the solvent S1 in the presence of water from such initial solution to obtain an aqueous solution of vanillin or of a vanillin derivative; b) a step of liquid/liquid extraction by bringing the aqueous solution obtained at the end of step a) into contact with a solvent S2, at a pH of greater than 8 and less than 10, to obtain an organic phase and an aqueous phase containing vanillin or a vanillin derivative and residual solvent S2; c) a step of precipitating, at a pH between 4 and 7.5, the vanillin contained in the aqueous phase obtained at the end of step b); and d) a step of isolating the vanillin or derivative thereof.

20 Claims, No Drawings

METHOD FOR PURIFYING VANILLIN BY LIQUID-LIQUID EXTRACTION

This application is a U.S. national stage entry under 35 U.S.C. §371 of International Application No. PCT/EP2012/075456 filed Dec. 13, 2012, which claims priority to French Application No. 11.61681 filed on Dec. 15, 2011, the whole content of this application being herein incorporated by reference for all purposes.

The present invention relates to a process for purifying vanillin and derivatives thereof, especially natural vanillin derived from fermentation. For the purposes of the present invention, the term "vanillin derivatives" particularly means vanillin glycoside.

Vanillin is a product widely used in many fields of application as a flavoring and/or fragrance. Thus, vanillin is abundantly consumed in the food and animal industry, but it also has applications in other fields, for instance pharmacy or perfumery. As a result, it is a mass-produced product.

In the context of the use of flavorings, it is increasingly important for the products used to be designated as "natural products". According to the regulations in Europe and in the United States, this means that the compound must be obtained via physical, enzymatic or microbiological processes and only from materials of plant or animal origin.

Thus, the studies concerning the purification of vanillin are centered on the use of natural, inexpensive and renewable raw materials. In this context, many patent applications concern the microbial or enzymatic production of vanillin. In general, a suitable precursor is transformed into vanillin via a microorganism or an enzyme. Among the precursors used, mention may be made especially of eugenol or related molecules (for example isoeugenol), ferulic acid, curcumin or Thai benzoin resin. However, the yields obtained for these processes are generally very low.

Among all these processes, an example that may be mentioned is the fermentation process described in patent application EP 0 761 817, describing the use of two strains of the genus *Amycolatopsis* for fermentation starting with ferulic acid.

There is still a large need to optimize the processes for preparing vanillin and derivatives thereof, especially natural vanillin.

An aim of the present invention is therefore to provide a process for purifying vanillin with a very high yield of vanillin, especially greater than 80%, or even greater than 90%.

An aim of the present invention is also to provide a process for purifying vanillin which makes it possible to obtain vanillin in a very high titer, especially greater than 97%, or even equal to 100%.

An aim of the present invention is also to provide a process for obtaining vanillin or derivatives thereof on an industrial scale in the form of commercialized product, the product thus obtained being natural within the meaning of the regulations.

The process according to the invention and the steps it implements are performed in accordance with flavoring regulation No. 1334/2008/EC.

The present invention thus relates to a process for purifying vanillin and derivatives thereof, starting with a solution of vanillin or of a vanillin derivative in a solvent S1 containing impurities, comprising the following steps:

a) a step of evaporation of solvent S1 in the presence of water to obtain an aqueous solution of vanillin or of a vanillin derivative;

b) a step of liquid/liquid extraction by placing the aqueous solution obtained after step a) in contact with a solvent S2, at a pH greater than 8 and less than 10, to obtain an organic phase and an aqueous phase containing vanillin or a vanillin derivative and residual solvent S2;

c) a step of precipitation, at a pH of between 4 and 7.5, of the vanillin or a derivative thereof contained in the aqueous phase obtained after step b), and d) a step of isolation of the vanillin or a derivative thereof.

The process of the present invention consists in purifying a solution of vanillin or of a derivative thereof containing impurities and a solvent (S1). Among these impurities, examples that may be mentioned include benzoic acid, vanillyl alcohol and guaiacol, and mixtures thereof. The vanillin solution may also optionally comprise other impurities, in particular vanillic acid, ferulic acid, compounds having a backbone with several phenyl groups, in general two or three phenyl groups, and also other heavy compounds. Said compounds containing two phenyl groups are referred to as dimers in the present invention. They are in particular diphenylmethane and derivatives thereof bearing substituents on the phenyl group(s). The phenyl groups present in the dimers are advantageously separated by a carbon-based chain or a chain containing a heteroatom, for example oxygen. Particular dimers comprising a ferulic unit are advantageously present in said vanillin solution. Dimers advantageously present in the vanillin solution have the formulae below:

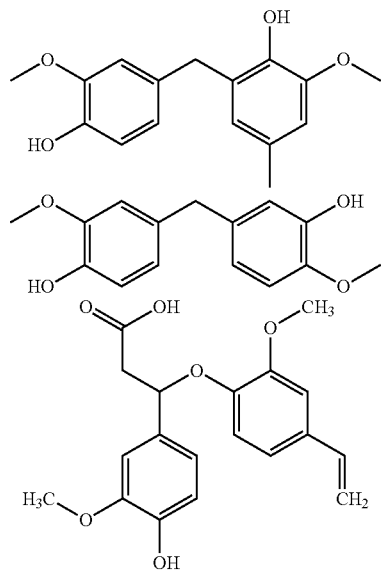

The impurities/vanillin weight ratio in the initial vanillin solution (crude vanillin) is generally between 0.10 and 0.35 and preferably between 0.15 and 0.35. Thus, the process of the present invention consists in removing these impurities in order to increase the final vanillin titer.

This vanillin solution to be purified is also referred to as the "starting vanillin solution" or the "initial vanillin solution" or the "crude vanillin".

The process according to the present invention makes it possible to obtain vanillin in solid form with a high titer, from an impure vanillin solution.

According to an advantageous embodiment of the process according to the present invention, the solution of vanillin in solvent S1 is derived from a fermentation process. A fermentation process that may especially be mentioned is the process described in EP 0 761 817.

According to one embodiment, the crude vanillin is a vanillin solution containing impurities formed during the fermentation of ferulic acid and the stabilization of the fermentation.

The process according to the invention is also suited to the purification of a vanillin derivative, for example vanillin glycoside, especially vanillin glycoside of natural origin extracted from vanilla pods.

The process according to the invention is performed according to a continuous procedure or a batchwise procedure.

When it is performed according to a batchwise procedure, the process according to the invention, in particular said steps a), b) and c), is preferentially performed in the same chamber, which is advantageously equipped with at least one distillation column on which is mounted at least one condenser.

Step a)—Evaporation of the Solvent S1 in the Presence of Water

The process of the present invention comprises a step a) that consists in removing by evaporation solvent S1 present in the initial vanillin solution or the solution of the vanillin derivative. In accordance with the process according to the invention, said evaporation step is performed in the presence of water. Preferably, solvent S1 has a boiling point of less than 100° C. or forms an azeotrope, with water, having a boiling point of less than 100° C.

Among the solvents S1, examples that may be mentioned include the organic solvents permitted by the regulations, such as alkyl acetates (ethyl acetate, propyl acetate, isopropyl acetate), MEK (methyl ethyl ketone), cyclohexane and dichloromethane. Solvent S1 may also be water.

Solvent S1 may also be a mixture of organic solvents, especially a mixture of organic solvents mentioned above or a mixture of water and of an organic solvent.

According to a preferred embodiment, solvent S1 is ethyl acetate.

Preferably, in the initial vanillin solution, the weight content of vanillin is between 10% and 60%, more preferentially from 10% to 40% and even more preferentially from 10% to 35% relative to the total weight of said solution. Step a) according to the present invention consists in removing solvent S1 to obtain an aqueous solution of vanillin in which the weight content of vanillin is preferably between 5% and 40%, more preferably between 5% and 35% and even more preferably between 5% and 25% relative to the total weight of said solution.

In accordance with the process according to the invention, the evaporation step a) is performed in the presence of water which is added to the initial vanillin solution before and/or during the implementation of said evaporation step.

According to a preferred embodiment, in the context of step a), solvent S1 of the crude vanillin is removed by evaporation, for example by distillation or by using an evaporator, in the presence of water, such that the vanillin and the impurities end up in the aqueous phase in soluble or insoluble form. In the case of an evaporation by distillation, solvent S1 may be distilled off at atmospheric pressure or under vacuum or alternatively at atmospheric pressure and then under vacuum.

The water may be added in one or more portions to the initial vanillin solution. It is preferable to use water fit for consumption (for example mains water). It is also possible to use recycled water fit for consumption, originating from the process according to the present invention (for example the washing waters, or the crystallization or precipitation mother liquors), as described hereinbelow.

The amount of water advantageously added to the initial vanillin solution before and/or during the implementation of said evaporation step a) is such that the weight content of vanillin in the aqueous solution obtained after step a) is advantageously between 5% and 40% by weight, very advantageously between 5% and 35% by weight and even more advantageously between 5% and 25% by weight relative to the total weight of said solution. Preferably, this weight content is from 10% to 15% by weight. The aqueous solution of vanillin obtained after said step a) contains the impurities formed during the fermentation and more generally those present in the vanillin solution subjected to the evaporation step.

Preferably, said evaporation step a) is performed at a temperature between 60 and 120° C. and more preferably between 80 and 120° C.

Step b)—Liquid/Liquid Extraction

After step a), the obtained aqueous solution of vanillin or of a vanillin derivative is subjected to a liquid/liquid extraction step under particular pH conditions.

The solvent used for this extraction step is referred to hereinbelow as solvent S2.

This step is performed at a controlled pH so as to separate certain impurities from vanillin by pKa difference. In particular, said step b) is performed so as to extract the impurities formed by species with a higher pKa than that of vanillin. These species are, for example, vanillyl alcohol, guaiacol and certain dimers or heavy compounds. The extraction according to said step b) may be total or partial. In accordance with said step b) of the process according to the invention, the pH is chosen so as to obtain a high yield of vanillin. Thus, the pH is strictly greater than 8 and less than 10.

During this step of extraction at controlled pH, the protonated species are extracted by solvent S2 and the organic layer predominantly comprises solvent S2. The vanillin then remains in the aqueous phase in the form of vanillate. For the rest of the process according to the present invention, the aqueous phase thus obtained is used, i.e., the steps subsequent to said liquid-liquid extraction step are performed using the aqueous phase containing the vanillate.

According to one embodiment, the extraction solvent S2 is different from solvent S1 present in the initial vanillin solution.

According to another embodiment, solvents S1 and S2 are identical. This embodiment is advantageous since it makes it possible in particular to perform only partial evaporation of said solvent according to said step a) of the process according to the invention and to use the non-evaporated part for performing said liquid-liquid extraction step.

In accordance with the process according to the invention, solvent S1 and solvent S2 are preferentially chosen from the solvents permitted by the regulations in force according to directive 2009/32/EC and directive 2010/59/UE concerning extraction solvents used in the manufacture of foodstuffs and ingredients thereof.

In accordance with said step b) of the process according to the invention, the extraction solvent S2 has no or very low to moderate solubility in water. More precisely, the maximum weight content of said solvent S2 in water is equal to 70 g/l. It goes without saying that solvent S2 is an organic solvent.

Preferably, solvent S2 is a solvent with low or very low solubility in water, i.e., its maximum weight content in water is equal to 50 g/l, and preferentially its maximum weight content in water is equal to 20 g/l. Solvent S2 may also be a water-insoluble solvent.

Said extraction solvent S2 advantageously has a boiling point less than 200° C. and preferentially less than 150° C.

Among the solvents S2 employed for the implementation of said step b) of the process according to the invention, examples that may be mentioned include dichloromethane, cyclohexane, ethyl acetate, propyl acetate, isopropyl acetate, n-butyl acetate, isoamyl acetate, methyl isobutyl ketone (MIBK), butanol, Rhodiasolv® RPDE (mixture of dimethyl adipate, dimethyl succinate and dimethyl glutarate), or a mixture of these solvents.

According to an advantageous embodiment, solvent S2 is chosen from food grade solvents. Preferably, solvent S2 is chosen from the group consisting of ethyl acetate, propyl acetate, isopropyl acetate, n-butyl acetate, isoamyl acetate and methyl isobutyl ketone (MIBK), and mixtures thereof. Even more preferably, solvent S2 is isopropyl acetate.

In order to obtain the particular pH conditions described above, according to one embodiment, step b) of the process according to the invention comprises the addition of a base, said base possibly being either a weak base or a strong base. Advantageously, said base is chosen from mineral bases, and more particularly water-soluble mineral bases. In particular, said base is chosen from the group consisting of alkali metal hydroxides, alkaline-earth metal hydroxides, alkali metal bicarbonates, alkaline-earth metal bicarbonates, alkali metal hydrogen carbonates, alkaline-earth metal hydrogen carbonates, alkali metal phosphates, alkaline-earth metal phosphates, alkali metal hydrogen phosphates and alkaline-earth metal hydrogen phosphates, and mixtures thereof. Very advantageously, said base is chosen from the following mineral bases: NaOH, KOH and $Na_2CO_3$. Preferentially, NaOH or KOH is used as base, and more particularly NaOH.

This base addition step makes it possible to adjust the pH for the liquid-liquid extraction step to a pH value greater than 8 and less than 10. Preferably, said extraction step according to step b) of the process according to the invention is performed at a pH of between 8.1 and 9.5, very preferentially between 8.3 and 9.5 and even more preferentially between 8.5 and 9. Controlling the pH for the implementation of said step b) leads, after the implementation of the process of the invention, to the production of a high-purity vanillin with an optimum yield.

In accordance with step b) of the process according to the invention, the addition of said base to the vanillin solution is performed before the addition of solvent S2 or after the addition of solvent S2. According to a preferred embodiment, the base is added rapidly to the vanillin solution, preferably in a single portion.

According to one embodiment of the process of the present invention, the base is added to the vanillin solution, optionally containing solvent S2, at a temperature from 15° C. to 60° C. and preferably between 30 and 50° C.

According to one embodiment of the process of the present invention, the base advantageously used for performing said step b) is diluted in water to a concentration from 5% to 30% by weight relative to the weight of said aqueous solution in which said base is diluted.

In accordance with the process according to the invention, said step b) is performed in a mass ratio between the mass of solvent S2 and the mass of vanillin advantageously from 0.2 to 3, preferably from 0.5 to 3 and preferentially from 0.6 to 1.2.

The liquid-liquid extraction step is preferably performed at atmospheric pressure and at a temperature between 15 and 40° C. and preferentially between 20 and 30° C. Preferably, said extraction step is preceded by a cooling step.

According to a particular embodiment, the base is added to the vanillin solution obtained after said step a) at a temperature from 15 to 60° C., preferably from 30° C. to 50° C., and the temperature is then lowered to a temperature preferentially between 15 and 40° C. and very preferentially between 20° C. and 30° C. before adding solvent S2 for the extraction.

After step b), an organic phase and an aqueous phase are obtained.

The organic phase contains some of the impurities, especially the guaiacol, vanillyl alcohol and dimers, and solvent S2, whereas the aqueous phase contains the vanillin in water, the rest of the impurities, for example ferulic acid, vanillic acid, benzoic acid and/or the particular dimers comprising a ferulic unit, and also residual solvent S2. The solvent S2 present in the organic phase, preferentially freed of impurities, is advantageously recycled upstream of said step b).

According to a batchwise procedure of the process according to the invention, the organic phase is then preferentially allowed to separate out by settling to recover the aqueous phase.

According to a continuous procedure of the process according to the invention, said liquid/liquid extraction step is advantageously performed by using a series of decanting mixers or at least one stirred, pulsed or packed liquid/liquid extraction column. It may also be performed continuously by using a static mixer and then a centrifugal separator for continuously separating the organic and aqueous phases.

According to an advantageous embodiment of the process according to the present invention, the aqueous phase obtained after the liquid-liquid extraction step is subjected to a step for removing residual solvent S2 ("stripping" step) so as to improve the quality of the vanillin obtained after the process of the invention.

Such a stripping step is performed under mild conditions, especially by injecting a gaseous fluid (for example water vapour or dinitrogen, preferably dinitrogen) and/or placing under vacuum of the chamber in which the process according to the invention is performed.

Preferentially, the stripping step is performed under vacuum. It is advantageously performed at a temperature between 20° C. and 50° C. The duration of said step is, for example, from 40 to 120 minutes.

Step c)—Precipitation

After step b), the vanillin or the vanillin derivative is present in aqueous solution in the form of vanillate.

This solution contains a large proportion of the impurities present in the crude vanillin, in particular the species whose pKa is less than that of vanillin. These species are, in particular, ferulic acid, vanillic acid, benzoic acid and particular dimers comprising a ferulic unit.

Step c) according to the process of the invention is performed at a controlled pH to lower the pH of the solution containing the vanillin in the form of vanillate. By lowering the pH, the vanillin precipitates out, the impurities remaining in the solution, referred to as the mother liquor.

Step c) of the process according to the invention is performed at a pH of between 4 and 7.5. These vanillin precipitation conditions make it possible to obtain a suitable yield of vanillin and also a minimum vanillin titer of 97% in the precipitate obtained after the precipitation step. The pH during the precipitation step is preferentially between 5 and 7, very preferentially between 5.7 and 6.5 and even more preferentially between 5.8 and 6.3.

Said precipitation step according to the process of the invention is performed using a weak or strong aqueous acid, which is introduced into said aqueous phase obtained after said step b) of the process according to the invention. Preferably, an acid that does not react with vanillin is used. Among the acids, mention may be made especially of acids whose formed salts are water-soluble. According to a preferred embodiment, the abovementioned precipitation step is performed in the presence of sulfuric acid.

According to one embodiment of the process according to the invention, said step c) is preferably performed at a temperature from 15° C. to 40° C. and preferentially from 25° C. to 40° C. Advantageously, said precipitation step is performed at atmospheric pressure. In accordance with said embodiment of the process according to the invention, said step c) comprises the addition of an acid, present in aqueous solution, to said aqueous phase obtained by decantation after said step b), preferentially followed by cooling of the aqueous medium from which the vanillin precipitates. The cooling is preferentially performed until a temperature advantageously less than or equal to 20° C. and preferentially less than or equal to 15° C., preferably a temperature between 5 and 15° C., is reached.

According to another embodiment of the process according to the invention, the addition of acid to said vanillin aqueous phase obtained from said step b) is preferentially performed at a temperature between 50 and 95° C. and very preferentially between 50 and 70° C. and at a pressure preferentially between 0.012 and 0.085 MPa and very preferentially between 0.012 and 0.03 MPa, and is followed by controlled cooling down to a temperature between 0 and 5° C. Said cooling is advantageously accompanied by controlled reduction of the pressure to a pressure of between 0.006 MPa and 0.008 MPa. The cooling is advantageously performed using an internal exchanger and/or by circulation of a heat-exchange fluid (in particular water) in a jacket with which is equipped the reactor in which said step c) is performed.

Step d)—Isolation of the Vanillin

The vanillin or the vanillin derivative obtained in the form of a precipitate after said step c) is isolated in step d) of the process according to the invention in order to improve its purification. Said step d) advantageously consists of at least one step of recovering solid vanillin on a filter or spin-dryer, followed by one or more steps of washing with water, preferentially followed by at least one drying step.

The solid vanillin obtained from said precipitation step c) is recovered on a filter or on a spin-dryer. In order to remove the residual impurities, especially mineral salts including sulfates, one or more washes with water may be necessary.

The vanillin is then advantageously dried, to be sold in its existing form. It may also be ground and/or recrystallized from water or from a water/alcohol mixture according to a known process.

The washing and drying steps performed in the context of the present invention are performed according to standard protocols that are well known to those skilled in the art.

Thus, according to one embodiment, the process of the present invention may comprise, after step d), a step of recrystallization of the vanillin from water or from an alcohol/water mixture. The vanillin thus obtained is in the form of white crystals.

In the context of the present invention, it is possible to further improve the yields by performing one or more additional recycling steps.

These additional steps consist in recycling various effluents obtained during the process of the invention, for example during the extraction, precipitation or washing step.

For example, it is possible to recycle the washing waters (i.e. the water recovered after the washing steps) and to use them as process water, i.e. with the water added before and/or the implementation of said evaporation step a) according to the process of the invention.

It is also possible to recover some of the vanillin contained in the mother liquors obtained after the precipitation step. This recovery may be performed either by modifying the pH followed by extraction with a solvent, or by reconcentration and precipitation, or by reconcentration and extraction.

It is also possible to recover, by washing, some of the vanillin contained in the organic phase obtained after the extraction step.

The examples below further illustrate the present invention, but are in no way limiting.

EXAMPLE 1

Vanillin Purification Process in Which the Extraction Step is Performed Using Dichloromethane (DCM)

1594 g of crude vanillin solution containing 19.3% by weight of vanillin, 1.4% by weight of vanillyl alcohol, 6 g (0.4% by weight) of benzoic acid and 18.5 g (1.1% by weight) of other impurities, especially guaiacol, dimers of diphenylmethane type and dimers bearing a ferulic unit, and also heavy compounds, were placed in a chamber equipped with a distillation column and a condenser. The solvent present in this solution was ethyl acetate and represented the weight remainder of the crude vanillin solution.

860 g of water were added to this solution, and the solvent consisting of ethyl acetate was then distilled off at atmospheric pressure and then under vacuum at a temperature equal to 100° C. and recovered as the head fraction (1404 g). Finally, 1800 g of water were added to the solution containing the vanillin after evaporation. An amount equal to 360 g of sodium hydroxide (22% by weight in water) was added to this vanillin solution, and a solution with a pH equal to 8.9 was then obtained. This solution was maintained at a temperature equal to 34° C. and was then allowed to cool to 24° C.

Next, 200 g of dichloromethane (DCM) were added and the extraction step was then performed at 24° C.

The organic phase thus obtained predominantly contained dichloromethane, but also 6 g of vanillin and 9 g of impurities, in particular vanillyl alcohol, guaiacol, dimers of diphenylmethane type and other heavy compounds.

The aqueous phase containing vanillin in the form of vanillate and residual dichloromethane was then stripped under vacuum (150 mmHg=0.2 bar) at 35° C. with injection of nitrogen for 2 hours.

Sulfuric acid ($H_2SO_4$, 50% by weight in water) was then added to the aqueous phase so as to obtain a solution with a pH=6.4 at 29° C. By lowering the temperature to 20° C., a precipitate was then obtained, which was filtered off to recover 2750 g of mother liquor containing 30 g of vanillin and impurities, in particular benzoic acid and particular dimers comprising a ferulic unit.

Finally, the solid obtained was washed twice with 750 g of water.

The vanillin thus obtained had a titer of 98.5% and contained less than 0.1% by weight of $Na_2SO_4$.

The overall yield ({purified vanillin/vanillin present in the crude vanillin solution} weight ratio) of vanillin without stream recycling was 85%.

With recycling of the washing waters and of part of the vanillin of the mother liquor, the yield was 94% with a final titer of 98%.

EXAMPLE 2

Vanillin Purification Process in Which the Extraction Step is Performed Using Isopropyl Acetate 200 g of crude vanillin solution containing 19.4% by weight of vanillin, 1.4% by weight of vanillyl alcohol, 1% by weight of benzoic acid and 5 g of other impurities, in particular vanillic acid, guaiacol, dimers of diphenylmethane type and particular dimers comprising a ferulic unit, and also heavy compounds, were used in a chamber equipped with a distillation column and a condenser. The solvent present in this solution was ethyl acetate and represented the weight remainder of the crude vanillin solution.

290 g of water were added to this solution, and the solvent consisting of ethyl acetate was then distilled off at atmospheric pressure at a temperature equal to 100° C. and recovered as the head fraction (180 g). 40 g of sodium hydroxide (22% by weight in water) were added to this aqueous solution of vanillin, and a solution with a pH equal to 8.6 was then obtained. This solution was maintained at a temperature equal to 40° C. and was then allowed to cool to 30° C.

Next, 39 g of isopropyl acetate were added and the extraction step was then performed at 30° C.

The organic phase thus obtained predominantly contained isopropyl acetate, but also 1.4 g of vanillin and 2 g of impurities, in particular vanillyl alcohol, guaiacol, dimers and heavy compounds.

The aqueous phase containing vanillin in the form of vanillate and residual isopropyl acetate was then stripped under vacuum (150 mmHg=0.2 bar) at 35° C. with injection of nitrogen for 2 hours. It was then cooled to about 25° C.

Sulfuric acid ($H_2SO_4$, 50% by weight in water) was then added to the aqueous phase so as to obtain a solution with a pH equal to 6 at 25° C. By lowering the temperature to 18° C., a precipitate was then obtained, which was filtered off to recover 290 g of mother liquor containing 2.5 g of vanillin and 6.4 g of impurities, in particular vanillic acid, benzoic acid and particular dimers comprising a ferulic unit.

Finally, the solid obtained was washed twice with 200 g of water.

The vanillin thus obtained had a titer of 99% and contained less than 0.1% of $Na_2SO_4$.

The overall yield of vanillin without stream recycling was 80%.

With recycling of the washes and of part of the vanillin of the mother liquor, the yield was 83% with a final titer of 99%.

EXAMPLE 3 (COMPARATIVE)

Vanillin Purification Process in Which the Extraction Step is Performed Using Isopropyl Acetate at a pH=10.5

200 g of crude vanillin solution containing 19.4% by weight of vanillin, 1.4% by weight of vanillyl alcohol, 1% by weight of benzoic acid and 5 g of other impurities, in particular vanillic acid, guaiacol, dimers of diphenylmethane type and particular dimers comprising a ferulic unit, and also heavy compounds, were used in a chamber equipped with a distillation column and a condenser. The solvent present in this solution was ethyl acetate and represented the weight remainder of the crude vanillin solution.

290 g of water were added to this solution, and the solvent consisting of ethyl acetate was then distilled off at atmospheric pressure at a temperature equal to 100° C. and recovered as the head fraction (182 g). 22% sodium hydroxide was added to this aqueous solution of vanillin, until a solution with a pH equal to 10.5 was obtained. This dark orange-brown solution was maintained at a temperature equal to 40° C. and was then allowed to cool to 30° C.

Next, 39 g of isopropyl acetate were added and the extraction step was then performed at 30° C.

The organic phase thus obtained predominantly contained isopropyl acetate and a few impurities, in particular vanillyl alcohol, guaiacol, dimers and other heavy compounds.

The aqueous phase containing vanillin in the form of vanillate and residual isopropyl acetate was then stripped under vacuum (150 mmHg=0.2 bar) at 35° C. with injection of nitrogen for 2 hours. It was then cooled to about 25° C.

Sulfuric acid ($H_2SO_4$, 50% by weight in water) was then added to the aqueous phase so as to obtain a solution with a pH equal to 6 at 25° C. No precipitate was obtained, even on lowering the temperature to 8° C. Analysis of the vanillin-rich solution (12.5% by weight) showed that the organic impurities were numerous: in particular, the presence of guaiacol, vanillyl alcohol, dimers and other heavy compounds was detected. Vanillic acid and benzoic acid were also present among the impurities in the vanillin solution obtained.

The acidification step therefore did not enable the purified vanillin to be isolated.

EXAMPLE 4 (COMPARATIVE)

Vanillin Purification Process in Which the Extraction Step is Performed Using Isopropyl Acetate at a pH=7.5

200 g of crude vanillin solution containing 19.4% by weight of vanillin, 1.4% by weight of vanillyl alcohol, 1% by weight of benzoic acid and 5 g of other impurities, in particular vanillic acid, guaiacol, dimers of diphenylmethane type and particular dimers comprising a ferulic unit, and also heavy compounds, were used in a chamber equipped with a distillation column and a condenser. The solvent present in this solution was ethyl acetate and represented the weight remainder of the crude vanillin solution.

290 g of water were added to this solution, and the solvent consisting of ethyl acetate was then distilled off at atmospheric pressure at a temperature equal to 100° C. and recovered as the head fraction. 22% sodium hydroxide was added to this aqueous solution of vanillin, until a solution with a pH equal to 7.5 was obtained. This solution was maintained at a temperature equal to 40° C. and was then allowed to cool to 30° C.

Next, 39 g of isopropyl acetate were added and the extraction step was then performed at 30° C.

The organic phase thus obtained (55 g) predominantly contained isopropyl acetate and 31% by weight of vanillin, and impurities, in particular vanillyl alcohol, guaiacol, dimers and other heavy compounds.

The aqueous phase containing vanillin in the form of vanillate and residual isopropyl acetate was then stripped under vacuum (150 mmHg=0.2 bar) at 35° C. with injection of nitrogen for 2 hours. It was then cooled to about 25° C.

Sulfuric acid ($H_2SO_4$, 50% by weight in water) was then added to the aqueous phase so as to obtain a solution with a pH equal to 6 at 25° C.

By lowering the temperature to 18° C., a precipitate was then obtained, which was filtered off to recover 242 g of mother liquor containing benzoic acid, vanillic acid and other impurities, especially the particular dimers comprising a ferulic unit.

Finally, the solid obtained was washed twice with 200 g of water.

The vanillin thus obtained (14 g) had a titer of 98.7%.

The overall yield ({purified vanillin/vanillin present in the crude vanillin solution} weight ratio) of vanillin without stream recycling was only 35%.

The invention claimed is:

1. A process for purifying vanillin and derivatives thereof, starting with an initial solution of vanillin or of a vanillin derivative in a solvent S1 containing impurities, comprising the following steps:
   a) a step of evaporation of said solvent S1 in the presence of water from said initial solution of said vanillin or of said vanillin derivative containing said solvent S1 to obtain an aqueous solution of said vanillin or of said vanillin derivative;
   b) a step of liquid/liquid extraction by placing the aqueous solution obtained after step a) in contact with a solvent S2, at a pH greater than 8 and less than 10, to obtain an organic phase comprising said solvent S2 and an aqueous phase containing said vanillin or said vanillin derivative and residual solvent S2;
   c) a step of precipitation, at a pH of between 4 and 7.5, of said vanillin or said derivative contained in the aqueous phase obtained after step b), and
   d) a step of isolation of said vanillin or said derivative thereof.

2. The process as claimed in claim 1, wherein said solvent S2 is different from said solvent S1.

3. The process as claimed in claim 1 wherein said solvent S1 has a boiling point of less than 100° C. or forms an azeotrope, with water, having a boiling point of less than 100° C.

4. The process as claimed in claim 1, wherein said solvent S1 is an organic solvent selected from the group consisting of alkyl acetates methyl ethyl ketone (MEK), cyclohexane, dichloromethane, and combinations thereof, or is a mixture of water and said organic solvent.

5. The process as claimed in claim 1, wherein said solvent S2 has a maximum solubility in water equal to 70 g/l.

6. The process as claimed in claim 1, wherein said solvent S2 is selected from the group consisting of dichloromethane; cyclohexane; ethyl acetate; propyl acetate; isopropyl acetate; n-butyl acetate; isoamyl acetate; methyl isobutyl ketone (MIBK); butanol; mixture of dimethyl adipate, dimethyl succinate and dimethyl glutarate; and a mixture of these solvents.

7. The process as claimed in claim 1, wherein said solvent S2 is isopropyl acetate.

8. The process as claimed in claim 1, wherein said step b) comprises adding a weak base or a strong base.

9. The process as claimed in claim 1, wherein said liquid-liquid extraction step b) is performed at a pH of between 8.5 and 9.

10. The process as claimed in claim 8, wherein said weak or strong base is diluted in water to a concentration from 5% to 30% by weight relative to the weight of said aqueous solution in which said weak or strong base is diluted.

11. The process as claimed in claim 1, wherein said step b) is performed with a weight ratio between said solvent S2 and said vanillin from 0.2 to 3.

12. The process as claimed in claim 1, wherein said aqueous phase obtained after the liquid-liquid extraction step b) is subjected to a step for removing said residual solvent S2.

13. The process as claimed in claim 1, wherein the pH during said precipitation step c) is between 5.7 and 6.5.

14. The process as claimed in claim 1, wherein said isolation step d) consists of at least one step of recovering solid vanillin on a filter or spin-dryer, followed by one or more steps of washing with water.

15. The process as claimed in claim 1, further comprising, after step d), a step of recrystallization of the vanillin from water or from an alcohol/water mixture.

16. The process as claimed in claim 1, wherein said solvents S1 and S2 are identical.

17. The process as claimed in claim 1, wherein said initial solution comprises a weight content in vanillin from 10 to 60% by weight.

18. The process as claimed in claim 1, wherein said initial solution comprises a weight ratio of impurities/vanillin between 0.10 and 0.35.

19. The process as claimed in claim 1, wherein said vanillin or said vanillin derivative in said aqueous solution obtained after step b) is in a vanillate form, and wherein said aqueous solution obtained after step b) contains impurities species whose pKa is below the pKa of vanillin.

20. The process as claimed in claim 1, wherein said impurities in said initial solution comprise benzoic acid, vanillyl alcohol, guaiacol, or mixtures thereof, and optionally further comprise species selected from the group consisting of vanillic acid, ferulic acid, dimers comprising two phenyl groups, dimers comprising a ferulic group, and heavy compounds; and wherein said liquid-liquid extraction step b) is carried out to separate some of these impurities by way of difference in their pKa from said vanillin.

* * * * *